(12) United States Patent
Al-Haik et al.

(10) Patent No.: US 8,426,489 B1
(45) Date of Patent: Apr. 23, 2013

(54) DENTAL COMPOSITIONS BASED ON NANOCOMPOSITES FOR USE IN FILLING AND DENTAL CROWNS

(75) Inventors: Marwan S. Al-Haik, Albuquerque, NM (US); Tariq A. Khraishi, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 489 days.

(21) Appl. No.: 12/638,566

(22) Filed: Dec. 15, 2009

Related U.S. Application Data

(60) Provisional application No. 61/201,874, filed on Dec. 15, 2008.

(51) Int. Cl.
- *A61L 24/02* (2006.01)
- *A61K 6/083* (2006.01)
- *A61C 13/087* (2006.01)
- *A61C 5/09* (2006.01)
- *A61C 5/10* (2006.01)
- *A61C 5/11* (2006.01)

(52) U.S. Cl.
USPC ........... 523/115; 523/113; 433/192; 433/218; 433/222.1; 433/223; 977/919

(58) Field of Classification Search ............... 523/115, 523/113; 433/192, 218, 222.1, 223; 977/919
See application file for complete search history.

(56) References Cited

U.S. PATENT DOCUMENTS

| | | | | |
|---|---|---|---|---|
| 5,624,976 | A * | 4/1997 | Klee | 523/116 |
| 2005/0239948 | A1 * | 10/2005 | Haik et al. | 524/496 |
| 2005/0260355 | A1 * | 11/2005 | Weber et al. | 427/566 |
| 2009/0176891 | A1 * | 7/2009 | Chogle et al. | 514/772.6 |

FOREIGN PATENT DOCUMENTS

WO    WO 2008066995 A2 * 6/2008

\* cited by examiner

*Primary Examiner* — Michael Pepitone
(74) *Attorney, Agent, or Firm* — MH2 Technology Law Group, LLP

(57) ABSTRACT

Present embodiments include composite dental materials for use in fillings and crowns, and methods of making the same. The composite materials can include biocompatible dental resin matrices and filler materials. The filler materials can include various types of magnetic nanoparticles. Additional embodiments include method of forming composite dental materials using a magnetic field and methods for forming aluminum oxide ($Al_2O_3$) nanoparticles. Other embodiments according to present teachings include methods for filling dental cavities and forming dental crowns.

13 Claims, 6 Drawing Sheets

DENTAL COMPOSITIONS BASED ON NANOCOMPOSITES FOR USE IN FILLING AND DENTAL CROWNS

RELATED APPLICATIONS

This application claims priority from U.S. Provisional Patent Application Ser. No. 61/201,874, filed Dec. 15, 2008, which is hereby incorporated by reference in its entirety.

FIELD OF THE INVENTION

The present embodiments relate to dental compositions and methods of making the same. Specifically, embodiments provide dental compositions with improved abrasion resistance, hardness and strength, and to methods of making the compositions of polymeric and/or ceramic matrices with nano-particles.

BACKGROUND OF THE INVENTION

This section introduces aspects that may be helpful in facilitating a better understanding of the invention. Accordingly, the statements of this section are to be read in this light and are not to be understood as admissions about what is in the prior art or what is not in the prior art.

The American Dental Association (ADA) has suggested that a pressing issue with restorative dental materials is the service life of the materials. The service life of the materials has been shown to be affected, for example, by the patient, the procedure and materials related issues. Examples of materials related issues can include; strength, hardness, toughness, wear resistance, tolerance to water, dimensional stability, and color stability.

Conventional dental fillings can be made out of fast-settings pastes obtained by mixing solid-liquid components. For example, the dental fillings can be set by an acid-base reaction (e.g., cements) or by polymerization (e.g., resins). An example standard filling can be made of zinc phosphate and can include zinc oxide powder and about a 50% phosphoric acid solution containing aluminum (Al) and zinc (Zn). This example mixed material can set into a hard, rigid cement by forming an amorphous zinc phosphate binder on a tooth. The bonding can arise from penetration into mechanically produced irregularities on the surface of a prepared tooth (e.g., due to surface roughening). However, some interfacial leakages can occur due to the cement's porosity.

Another example of filling material is zinc polyacrylate (polycarboxylate) cement, which can be formed from zinc oxide and a polyacrylic acid solution. The zinc ion can form a crosslink polymer structure by crosslinking carboxyl groups to calcium (Ca) ions on the surface of a tooth. Glass ionomer cements can also based on polyacrylic acid or its copolymers with maleic or itaconic acids and can utilize calcium aluminosilicate glass powder rather than zinc oxide. Glass ionomer cements can be set by crosslinking polyacid with Ca and Al ions from the glass.

Another type of dental filling material can be resins, which are fluid monomers systems based on, for example, aromatic or urethane dimethacrylates. Ceramic fillers can be present to yield a composite material. The resin can be filled with inorganic materials, for example, quartz, borosilicate glass, lithium aluminum silicate, barium aluminum silicate, barium fluoride, ceramic materials, etc., to form composite materials. These inorganic fillers can range in size from about 0.04 to about 10 μm. The composite materials can be mixed with a hardening catalyst or photoinitializer, and then cured using UV-light. Because these composites have a relatively low viscosity (since they have a small amount of filler compared to the resin) the composites can be applied to the necessary tooth regions easily and can fill in smaller regions such as cracks in the tooth. However, since the composites have less filler than other dental materials, shrinkage can occur during curing, which can make these composites inappropriate for larger cavities. Two-component resins can polymerize on mixing through a two part organic peroxide-tertiary amine initiator-activator system in about three minutes. Materials containing diketone initiators can achieve polymerization in about thirty seconds by exposure to visible (blue) light energy.

In view of the above, there has been a growing interest in producing new dental fillers based on nanocomposites that will improve upon the products currently available for dental restoration. Such new dental fillers would be tailored to have superior mechanical performance, by controlling, for example, microstructure, size and distribution of nanofillers.

SUMMARY

Embodiments according to the present teachings include composite materials, methods of making the composite materials, and methods of using the composite materials. In one embodiment, magnetic nanoparticles, including a magnetic core and a biocompatible outer sheath surrounding the magnetic core.

Another embodiment according to present teachings provides a composite material including a biocompatible dental resin matrix and filler including a plurality of magnetic nanoparticles. The biocompatible dental resin is selected from aromatic or urethane dimethacrylate resins. The plurality of magnetic nanoparticles can be selected from single-wall carbon nanotubes (SWCNTs), multi-wall carbon nanotubes (MWCNTs), graphite nanoparticles, carbide nanoparticles, oxide nanoparticles, and combinations thereof. The plurality of magnetic nanoparticles can further include a magnetic core with a biocompatible polymer sheath surrounding the magnetic core and carbon nanotubes. In further embodiments, the plurality of magnetic nanoparticles can include randomly dispersed carbon nanotubes in the biocompatible dental resin or can be magnetically aligned carbon nanotubes in the biocompatible dental resin.

Another embodiment includes a method of forming a composite material, including applying a permanent magnetic field to a composite material including magnetic nanoparticles dispersed in a biocompatible dental resin. The magnetic field can be about 0.5 to about 1 Tesla and can align the magnetic nanoparticles to one another along an axial direction. The method can further including curing the composite material by applying ultra-violet (UV) energy.

Another embodiment includes a method of filling a dental cavity, including applying a dental composite to at least one tooth, where the composite can include a biocompatible dental resin matrix and a filler. The filler can include a plurality of magnetic nanoparticles and a magnetic field can be applied to the at least one tooth to axially align the magnetic nanoparticles. The dental composite can also be cured. A portion of the cured dental composite can also be optionally removed.

A further embodiment can include a method of forming a dental crown. The method can includes mixing carbon nanotubes with a ceramic powder, filling a dental crown mold with the mixed carbon nanotubes and ceramic powder and pressing the mixture using Hot Isostatic Pressing (HIP). The pressed mixture can then be sintered.

Additional embodiment can include a method of forming nanoparticle. In this method a precursor can be excited by ultrasonic energy, passing an aerosol carrier gas mixture through the excited precursor to form an aerosol, and applying microwave power to a plasma torch can be provided. The aerosol can then be passed through the microwave powered plasma torch to form the nanoparticles. The precursor can be aluminum, the carrier gas mixture can be a mixture of argon and oxygen through the excited precursor, and the plasma torch can be an argon plasma torch.

BRIEF DESCRIPTION OF THE DRAWINGS

Some embodiments of methods in accordance with embodiments of the present invention are now described, by way of example only, and with reference to the accompanying drawings, in which.

DESCRIPTION OF THE EMBODIMENTS

Figure 1:
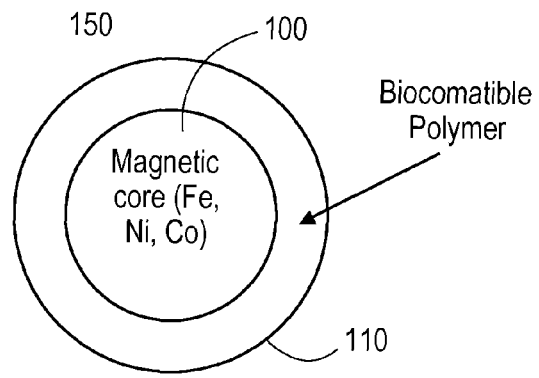
FIG. 1 shows a diagram of a magnetic nanoparticle coated and/or sheathed with a biocompatible polymer according to present teachings.

Reference will now be made in detail to the present embodiments (exemplary embodiments) of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

For simplicity and illustrative purposes, the principles of the present invention are described by referring mainly to exemplary embodiments thereof. However, one of ordinary skill in the art would readily recognize that the same principles are equally applicable to, and can be implemented in, all types of secure distributed environments and that any such variations do not depart from the true spirit and scope of the present invention. Moreover, in the following detailed description, references are made to the accompanying figures, which illustrate specific embodiments. Electrical, mechanical, logical and structural changes can be made to the embodiments without departing from the spirit and scope of the present invention. The following detailed description is, therefore, not to be taken in a limiting sense and the scope of the present invention is defined by the appended claims and their equivalents.

As used herein and unless otherwise specified, the term magnetic is intended to include materials that have at least some magnetic properties including, for example, ferromagnetic, paramagnetic, etc. Also, as used herein and unless otherwise specified, the term composite is intended to include any and all engineered materials made from two or more constituent materials with significantly different physical or chemical properties which remain separate and distinct on a macroscopic level within the finished structure.

As used herein and unless otherwise specified, the term dental cavity is intended to include any type of hole, cavity, crack, etc., formed in a tooth of an animal or human and as used herein and unless otherwise specified, the term dental crown is intended to include any shape that can be used to repair and/or restore a tooth of an animal or human.

As used herein and unless otherwise specified, the term "nanotubes" refers to elongated materials (including organic and inorganic materials) having at least one minor dimension, for example, width or diameter, of about 1000 nanometers or less. In various embodiments, the minor dimension can be less than 500 nm or less than about 100 nm. In embodiments according to present teachings, the nanotubes can also have an aspect ratio (e.g., length:width and/or major dimension: minor dimension) greater than 10.

Although the term "nanotubes" is referred to throughout the description herein for illustrative purposes, it is intended that the term also encompass other elongated structures of like dimensions including, but not limited to, nanoshafts, nanopillars, nanowires, nanorods, and nanoneedles and their various functionalized and derivatized fibril fauns, which include nanofibers with exemplary forms of thread, yarn, fabrics, etc.

The term "nanotubes" can also include single wall nanotubes such as single wall carbon nanotubes (SWCNTs), multi-wall nanotubes such as multi-wall carbon nanotubes (MWCNTs), and their various functionalized and derivatized fibril forms such as nanofibers. Furthermore, the term "nanotubes" can include modified nanotubes from all possible nanotubes described there above and their combinations. The modification of the nanotubes can include a physical and/or a chemical modification. The nanotubes can have various cross sectional shapes, such as, for example, rectangular, polygonal, oval, or circular shape. Accordingly, the nanotubes can have, for example, cylindrical 3-dimensional shapes.

In some embodiments, the nanotubes can be obtained in low and/or high purity dried paper forms or can be purchased in various solutions. In other embodiments, the nanotubes can be available in the as-processed unpurified condition, where a purification process can be subsequently carried out.

Present embodiments include composite dental materials for use in fillings and crowns, and methods of making the same. The composite materials can include biocompatible dental resin matrices and filler materials. The filler materials can include various types of magnetic nanoparticles. Additional embodiments include method of forming composite dental materials using a magnetic field and methods for forming aluminum oxide ($Al_2O_3$) nanoparticles. Other embodiments according to present teachings include methods for filling dental cavities and forming dental crowns.

FIG. 1 shows a general view of magnetic nanoparticles 150 according to present teachings. In the embodiment shown, the nanoparticles 150 can include a magnetic core 100, for example, based on Iron, Nickel, Cobalt, and/or their derivative compounds that are nontoxic and biocompatible, etc., with a surrounding and/or sheathing of biocompatible polymer 110, for example, silicon oxide, yttrium oxide, etc. The magnetic cores 100 of nanoparticles 150 can also include graphite nanoparticles, silicon carbide nanoparticles (or, e.g., other carbides) and/or aluminum oxide ($Al_2O_3$) nanoparticles (or, e.g., other oxides). Embodiments including aluminum oxide can be of interest because aluminum oxide can be used in a wide variety of areas due to many beneficial properties and several existing crystalline phases. For example aluminum oxide can exist in a number of crystalline phases (polymorphs) including, for example, γ, d, θ, and a. Aluminum oxide can be used as wear-resistant coatings due to its elevated hardness, thermal stability, structural stability, insulating properties, and transparency.

Figure 2:
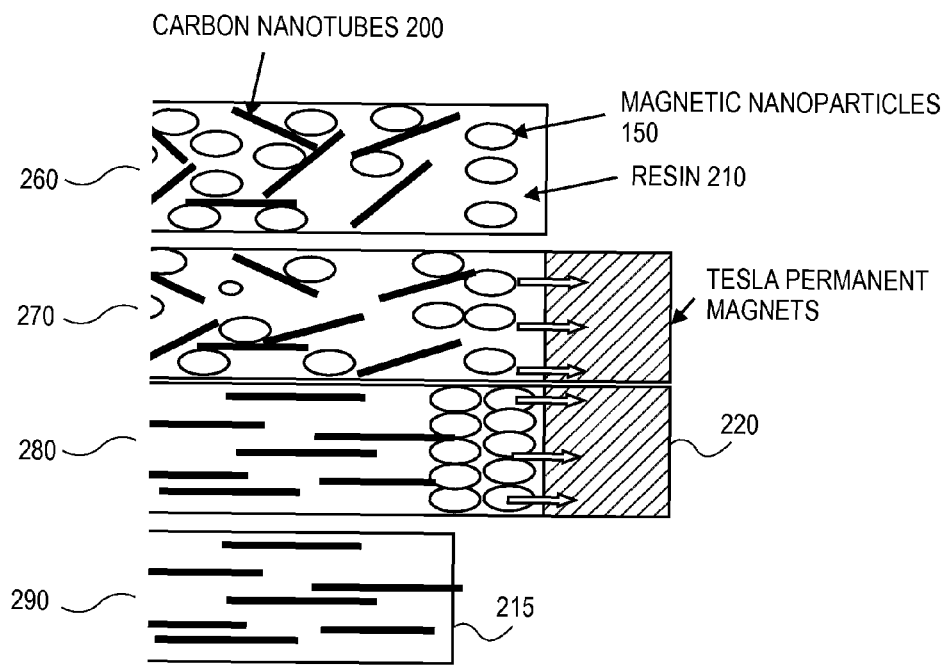
FIG. 2 shows a diagram of a dental composite including carbon nanotubes and magnetic nanoparticles in a polymer resin, and a permanent magnet of about 1 Tesla according to present teachings.

FIG. 2 shows example embodiments of composite dental materials 260-290 that can be used in dental fillings and/or crowns. The dental composite material 260-290 generally can include resin 210 (e.g., epoxy systems, polymer bases, etc.) that can be cured by ultraviolet light (UV) (not shown) to form composite material 280-290 having a cured polymer matrix (not shown). The resin 210 can be mixed with filler, which can include mixtures of, for example, single-wall carbon nanotubes (SWCN) 200, multi-wall carbon nanotubes (MWCNs) 200, the magnetic nanoparticles 150 shown in FIG. 1, etc.

As shown in 260, the mixture of carbon nanotubes 200 and magnetic nanoparticles 150 can be randomly dispersed in resin 210 by mixing and optionally applying ultrasonic energy (not shown) to the mixture. The ultrasonic energy can assist the dispersion of the nanoparticles 150 and the nanotubes 200 within the resin 210. If an epoxy based system is used for the resin 210, then a hardener component (not shown) can be mixed with the resin 210, magnetic nanoparticles 150, and nanotubes 200 prior to curing.

In FIG. 2, a permanent magnet 220 (e.g., a tesla permanent magnet) is shown being applied to composite material 270 and 280. The permanent magnet 220, can induce a magnetic field of about 0.5 to about 0.1 Tesla around composite material 270/280. As shown the carbon nanotubes 200 and the magnetic nanoparticles 150 magnetically align along an axial direction based on the applied magnetic field (shown as arrows). Also shown in FIG. 2 is that the magnetic nanoparticles 150 can move more rapidly toward the external magnet force, due in part to their high magnetic susceptibility. Once a predetermined majority of the magnetic nanoparticles 150 have moved towards the external magnet 220, UV energy (not shown) can be applied to composite material 280 to cure and therefore lock the carbon nanotubes 200 in their aligned positions. After curing, the magnetic nanoparticles 150 can be removed (not shown) resulting in composite material 290. The magnetic nanoparticles 150 can be, for example, machined, etched, polished, etc., or otherwise removed to leave composite material 290 including a cured polymer matrix 215 including axially aligned carbon nanotubes 200.

Figure 3:
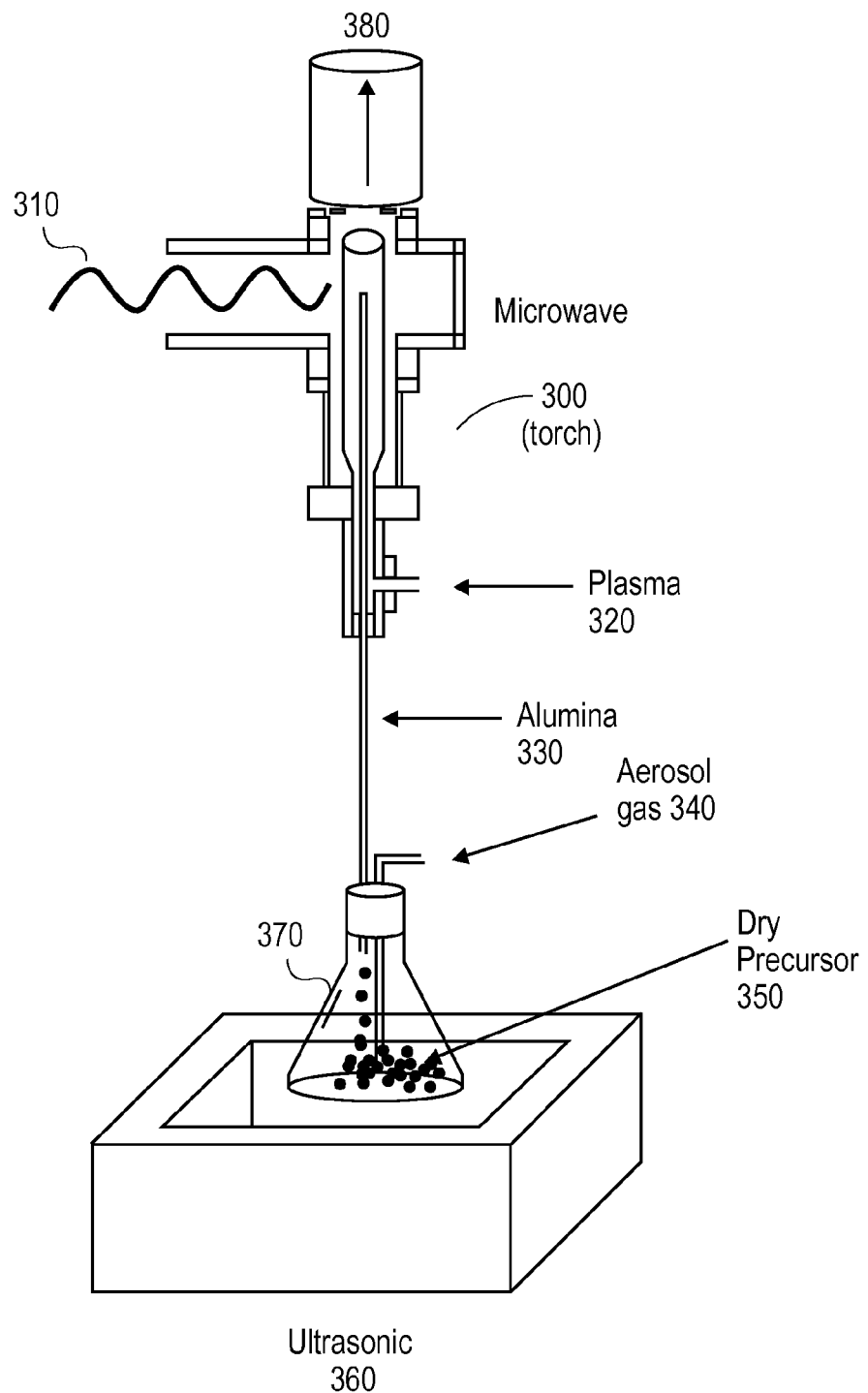
FIG. 3 shows a schematic of a torch apparatus for synthesis of Aluminum oxide nanoparticles according to present teachings.

A microwave powered argon plasma torch apparatus 305 is shown in FIG. 3. The plasma torch apparatus 305 can be used to form embodiments of magnetic nanoparticles of aluminum oxide according to present teachings. As shown in FIG. 3, low powered microwave power can be directed down microwave guide 310. At the end of the microwave guide 310 a plasma torch 300 is attached. A plasma gas (e.g., argon (Ar) 320 can be flowed in at the bottom of plasma torch apparatus 305 to create a plasma. A dry precursor (e.g., aluminum) 350 can have ultrasonic energy applied to through the use of, for example, an ultrasonic plate 360. The dry precursor 350 is held within an enclosed container 370 through which a gas 340 is distributed to form an aerosol (not shown) of the dry precursor 350. The aerosol of the gas 340 and the dry precursor 350 can then be passed through the plasma to form alumina 330. Plasma can vaporize the aerosol and form aluminum oxide nanoparticles on the far side 380 of the plasma torch apparatus 305. The aluminum oxide nanoparticles can then be carried to filters (not shown) with nano-sized pores by a slight vacuum of, for example, 605 ton, in order to separate different size nanoparticles. Using this embodiment, collected particles can be produced at a rate of about 250 mg/hr to about 7464 mg/hr. The resulting nanoparticles from the process discussed with reference to FIG. 3 can be spherical or randomly shaped, which can be anisotropic (e.g., that the nanoparticles will be equally strong regardless of the particle orientation) and range from about 10 nm to about 300 nm in diameter, more specifically, from about 10 nm to about 75 nm.

Figure 4:
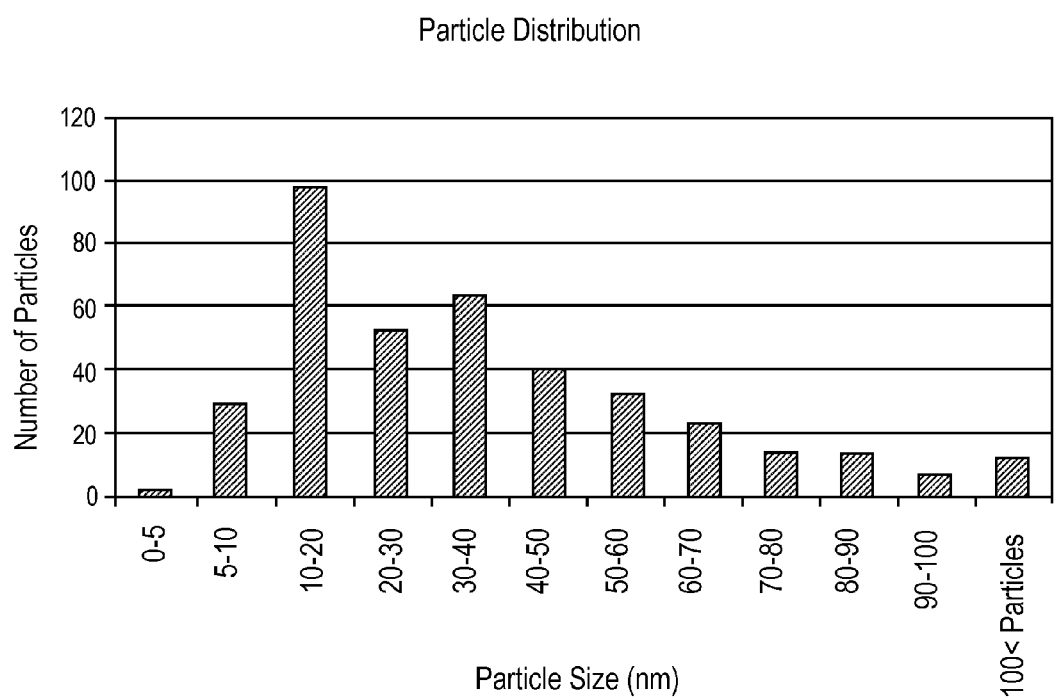
FIG. 4 shows an example particle spread of alumina particles made using the apparatus of FIG. 3.
Figure 5:
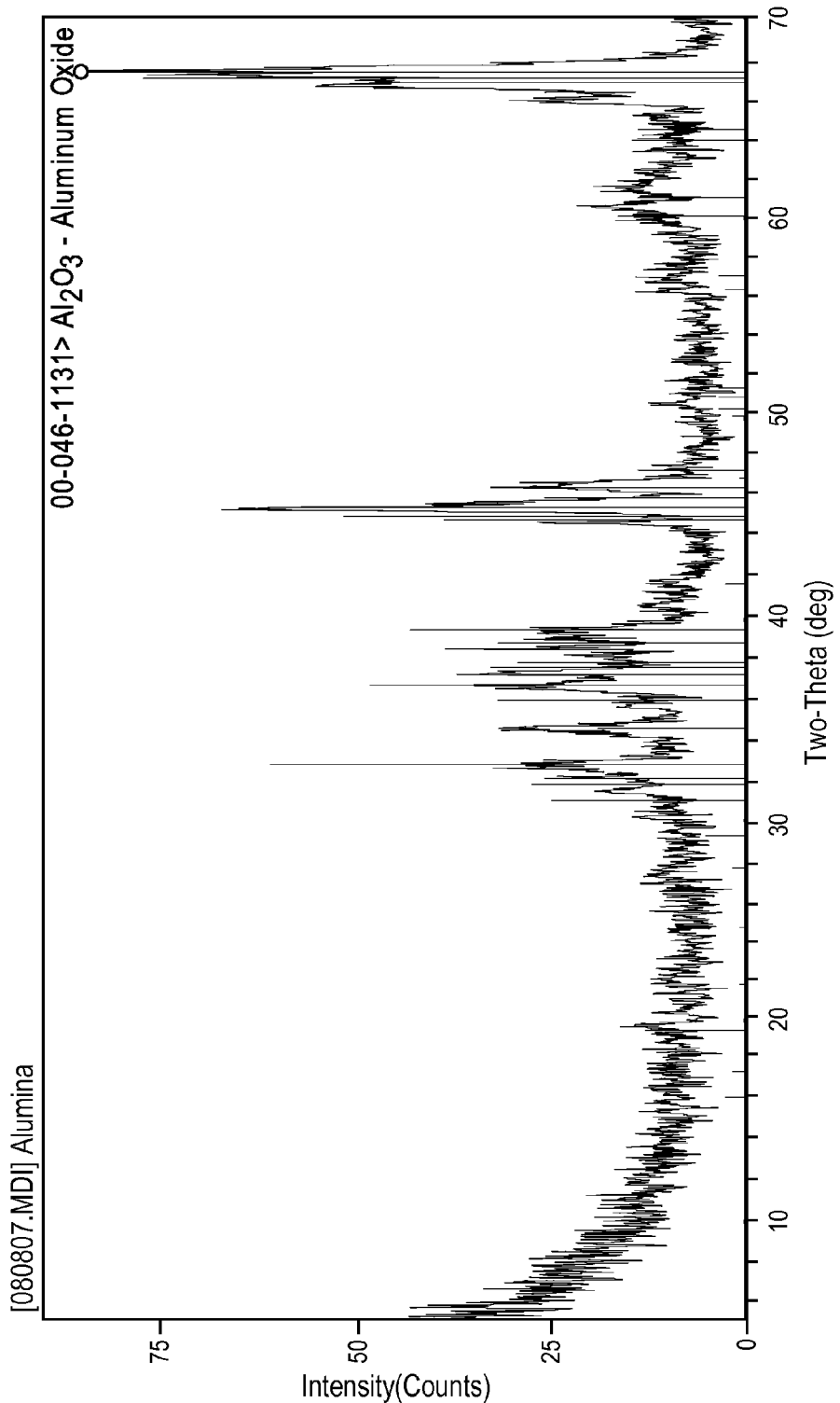
FIG. 5 shows results from x-ray diffraction of the Aluminum oxide nanoparticles according to present teachings.

FIG. 4 shows a graph illustrating example particle distribution of the nanoparticles formed by the apparatus of FIG. 3. A count of 400 particles can be used for the particle distribution analysis. As shown, the nanoparticles spread can be greater than about 100 nm and the average size of the particles can be about 34.81 nm. FIG. 4 also shows that the nanoparticle size distribution ranges from about 1 to about 70 nm. X-ray diffraction can also be used to characterize the compositions of the nanoparticles synthesized formed by the apparatus of FIG. 3. FIG. 5 shows example x-ray diffraction results. The x-ray diffraction graph shows that the plasma torch apparatus 305 can synthesize a majority of pure grade tetrahedral δ phase aluminum oxide.

Figure 6:
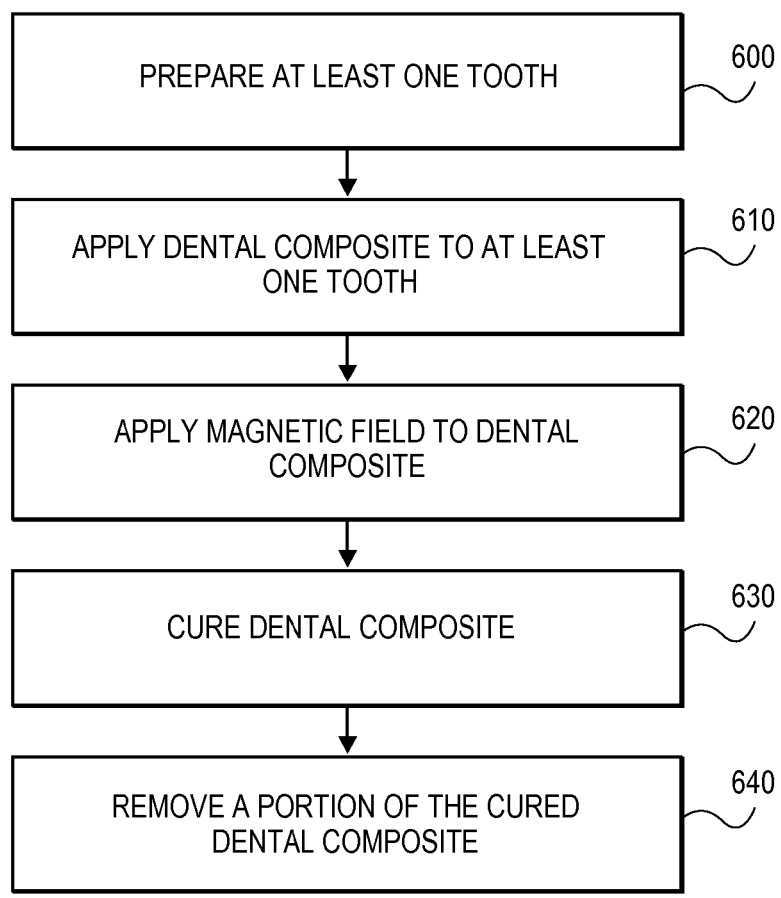
FIG. 6 is a flow chart showing a method of filling a dental cavity according to present teachings.

Another embodiment according to present teachings includes a method of filling a dental cavity as shown in the flow chart of FIG. 6 and with reference to FIG. 2. In step 600 a surface of a tooth, including the enamel can be prepared by, for example, etching, priming, etc. After step 600, the dental composite 260 (a mixture of resin and filler) can be applied to the prepared tooth. The tooth can have a cavity or crack and more than one tooth can be filled at one time. In step 620 a relatively weak magnetic field, e.g., about 1 tesla, can be applied to the tooth having been filled. As shown in FIG. 2, the dental composite 260 will transform through composite 270 to 280 composite due to the applied magnetic field. When the nanoparticles 150 and carbon nanotubes 200 have axially aligned, an external UV source can be applied to cure the composite 280 in step 630. As illustrated in FIG. 2, a person performing the filling could also notice that a majority of the nanoparticles 150 are floating on the surface of the composite 280 closest to the magnet 220. After curing, the nanoparticles 150 on the top surface of composite 280 can be optionally machined out forming composite 290 in step 640. Also, an optional layer of resin (not shown) can be used after preparing the tooth but before the dental composite 260 is applied in order to increase the adhesion of composite 260.

Figure 7:
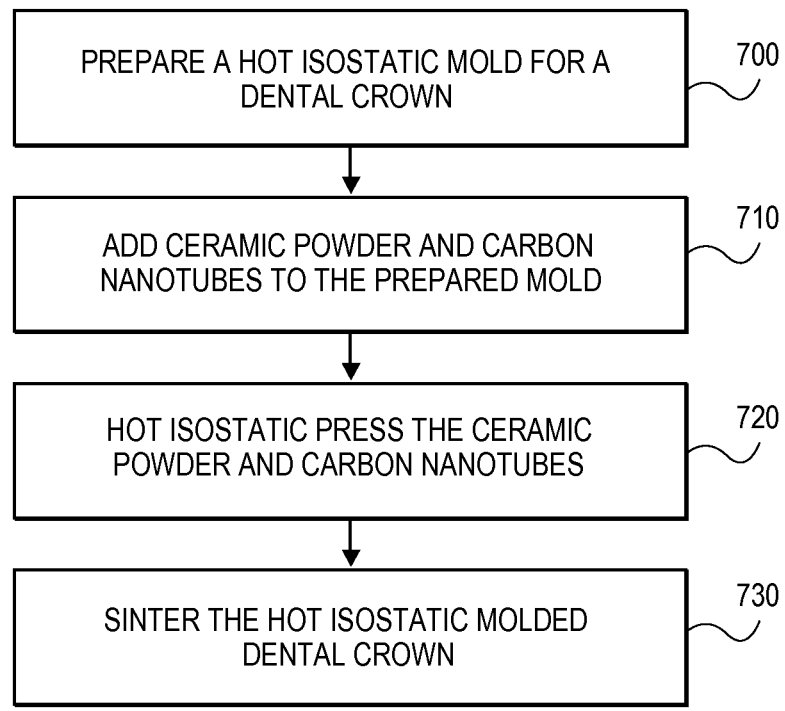
FIG. 7 is a flow chart illustrating a method of making a dental crown according to present teachings.

In another embodiment shown by the flow chart of FIG. 7, a crown can be made by using Hot Isostatic Pressing (HIPing) of a mixture of ceramic powder and carbon nanotubes. For example, a hot isostatic mold for a dental crown can be prepared (e.g., cleaning priming, etc.) in step 700. A mixture of ceramic powder and carbon nanotubes can then be added to the mold in step 710. In step 720 HIPing can then be used to form a molded crown, which can then be sintered at a temperature lower than the melting point of both ingredients in step 730. The HIPing parameters can be materials dependant and, for example, the pressure can be more than the yield strength of the material and the temperature cannot exceed about 50% of the melting point of the corresponding materials.

As discussed above, embodiments according to present teachings include composite materials, methods of making the same, methods of filling dental cavities, and methods of forming dental crowns. While the present teachings have been illustrated with respect to one or more implementations, alterations and/or modifications can be made to the illustrated examples without departing from the spirit and scope of the appended claims.

In addition, while a particular feature of the present teachings may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, 40, −20, −30, etc.

It is noted that, as used in this specification and the appended claims, the singular forms "a," "an," and "the," include plural referents unless expressly and unequivocally limited to one referent. Thus, for example, reference to "a particle" includes two or more different particles. As used herein, the term "include" and its grammatical variants are intended to be non-limiting, such that recitation of items in a list is not to the exclusion of other like items that can be substituted or other items that can be added to the listed items.

It will be apparent to those skilled in the art that various modifications and variations can be made in the devices and methods of the present disclosure. Other embodiments of the disclosure will be apparent to those skilled in the art from consideration of the specification and practice of the embodiments disclosed herein. It is intended that the specification and examples be considered as examples only.

What is claimed is:

1. A composite material comprising:
   a biocompatible dental resin matrix;
   a plurality of carbon nanotubes disposed in the biocompatible dental resin matrix; and
   a plurality of magnetic nanoparticles disposed in the biocompatible dental resin matrix, wherein each of the plurality of magnetic nanoparticles comprises (a) a magnetic core and (b) a sheath surrounding the magnetic core, and wherein the sheath comprises silicon oxide or yttrium oxide.

2. The composite material of claim 1, wherein the biocompatible dental resin comprises an aromatic dimethacrylate resin.

3. The composite material of claim 1, wherein the magnetic core comprises iron, nickel, or cobalt.

4. The composite material of claim 1, wherein the plurality of magnetic nanoparticles and the plurality of carbon nanotubes are randomly dispersed in the biocompatible dental resin matrix.

5. The composite material of claim 1, wherein the plurality of carbon nanotubes in the biocompatible dental resin are axially aligned.

6. A method of forming a dental composite material, comprising:
   forming the composite material according to claim 1; and
   applying a magnetic field to the composite material.

7. The method of claim 6, wherein applying a magnetic field further comprises:
   applying a magnetic field of about 0.5 to about 1 Tesla.

8. The method of claim 7, wherein applying a magnetic field further comprises:
   aligning the magnetic nanoparticles to one another along an axial direction.

9. The method of claim 6, further comprising:
   curing the composite material by applying ultra-violet (UV) energy.

10. A method of filling a dental cavity, comprising:
    applying the composite material according to claim 1 to at least one tooth;
    applying a magnetic field to the at least one tooth to axially align the plurality of magnetic nanoparticles; and
    curing the dental composite.

11. The method of claim 10, further comprising:
    removing a portion of the cured dental composite.

12. The method of claim 10, further comprising:
    preparing the at least one tooth for the dental composite.

13. The method of claim 12, wherein preparing the at least one tooth comprises:
    cleaning the at least one tooth; and
    priming the at least one tooth.

* * * * *